United States Patent [19]

Brown et al.

[11] 4,230,717

[45] Oct. 28, 1980

[54] INDOMETHACIN-ANTIHISTAMINE COMBINATION FOR GASTRIC ULCERATION CONTROL

[76] Inventors: Alan M. Lovelace, Administrator of the National Aeronautics and Space Administration, with respect to an invention of Patricia A. Brown, Menlo Park, Calif.; Joan Vernikos, London, England

[21] Appl. No.: 974,476

[22] Filed: Dec. 29, 1978

Related U.S. Application Data

[63] Continuation-in-part of Ser. No. 850,504, Nov. 10, 1977.

[51] Int. Cl.³ .............................................. A61K 31/40
[52] U.S. Cl. ................................................... 424/274
[58] Field of Search ......................................... 424/274

[56] References Cited

U.S. PATENT DOCUMENTS

| | | | |
|---|---|---|---|
| 3,927,213 | 12/1975 | Lippmann | 424/273 |
| 3,988,466 | 10/1976 | Takagiet | 424/274 |

OTHER PUBLICATIONS

Brown et al., Life Sciences 18, pp. 339–344, (Pergamon Press, 1976).
International Symposium on Histamine $H_2$-Receptor Antagonists, London 1 & 2, Oct. 10–73.

*Primary Examiner*—Stanley J. Friedman
*Attorney, Agent, or Firm*—Armand McMillan; John R. Manning; Darrell G. Brekke

[57] ABSTRACT

An anti-inflammatory and analgesic composition containing indomethacin and an $H_2$ histamine receptor antagonist in an amount sufficient to reduce gastric distress caused by the indomethacin. Usable antagonists are metiamide and cimetidine.

2 Claims, 5 Drawing Figures

INDOMETHACIN-ANTIHISTAMINE COMBINATION FOR GASTRIC ULCERATION CONTROL

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

RELATED APPLICATION

This application is a continuation-in-part of Application Ser. No. 850,504, filed on Nov. 10, 1977.

BACKGROUND OF THE INVENTION

1. Field of the Invention

This invention relates to indomethacin, a relatively new compound that has found wide use as an anti-inflammatory agent, an antipyretic and an analgesic. More particularly, the invention relates to the the elimination of the undesirable gastric side effects caused by the compound.

2. The Prior Art

Non-steroidal anti-inflammatory agents, such as aspirin and indomethacin, have long been known to be ulcerogenic, particularly in conjunction with other influences, such as stress. One of the most successful efforts to combat this undesirable side effect of an otherwise very useful compound has been the use of metiamide with aspirin, disclosed by Brown et al. in "Histamine H$_2$ Receptor: Involvement in Gastric Ulceration, " Life Sciences 18, pages 339-344 (Pergamon Press, 1976). Interestingly, this compound metiamide, which was found to reliably reduce ulceration produced by stress alone, or by a combination of stress and aspirin, is known to be an H$_2$ histamine receptor antagonist. On the other hand, H$_1$ receptor antagonists, such a- pyrilamine, a compound which has been heretofore administered with aspirin for purposes other than that of present concern, have been found by the same workers to be ineffective for the control of gastric ulceration.

As to indomethacin, attempts to combat the gastrointentinal side effects that it induces in a patient have resulted in the discovery that the undesirable effects can be controlled by the administration of certain prostaglandin substances (Lippmann, U.S. Pat. No. 3,927,213) and certain amino acids (Takagi et al., U.S. Pat. No. 3,988,466). It should be noted also that indomethacin itself can be used to control, inter alia, the peptic ulcer complications often produced by anti-inflammatory adrenocortical steroids (Winter, U.S. Pat. No. 3,461,208).

SUMMARY OF THE INVENTION

It is an object of the present invention to provide pharmaceutical preparations containing indomethacin, which do not cause gastric distress in a patient subject to stress. A more specific object is to provide anti-inflammatory, antipyretic and analgesic compositions containing indomethacin and at least one other compound which can markedly reduce or eliminate gastric ulceration that indomethacin generally causes in patients under stress.

These objects have been accomplished by formulating preparations which include indomethacin and an antihistamine component consisting of one or more H$_2$-receptor antagonists such as metiamide and cimetidine.

DETAILED DESCRIPTION OF THE INVENTION

Figure 1:
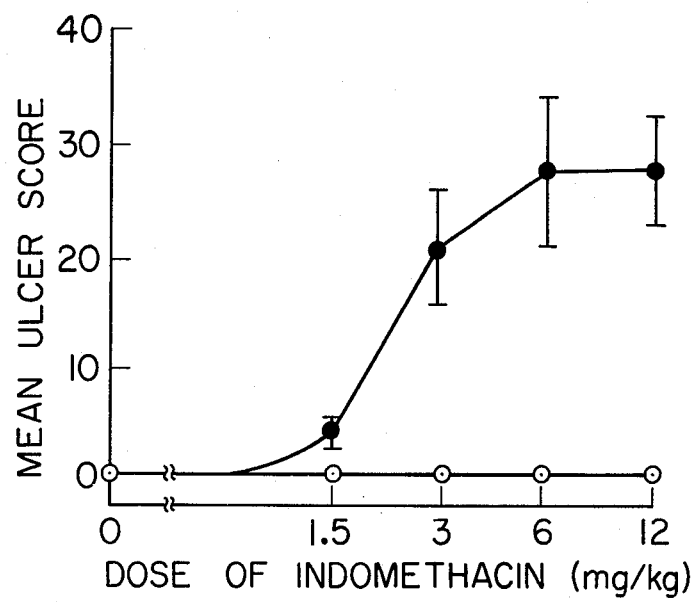
FIG. 1 of the drawings depicts the ulcerogenic properties of indomethacin in the presence and in the absence of stress.

Indomethacin, i.e., 1-(p-chlorobenzoyl)-5-methoxy-2-methyl-3-indolylacetic acid, has found much acceptance in pharmaceutical therapy for its anti-inflammatory, antipyretic, and analgesic properties. In some of these capacities, the compound may have to be taken for long periods and in large doses, and under such a regime, it often gives rise to gastric ulcers in subjects under stress.

It has now been discovered that the gastric ulcers caused by the ingestion of indomethacin by a subject under stress can be significantly reduced by administering an H$_2$-receptor antagonist, e.g., metiamide and cimetidine.

The indomethacin and the antihistamine may be administered individually or together in the same dosage unit, such as tablets, capsules, liquids and so on. Suitable diluents or even additional active ingredients can be present in such preparations, if desired. In any event, the anti-inflammatory drug is employed in its usual dosage, i.e., about 25 mg to 200 mg daily, while the dosage for the antihistamine can range from 200 mg to 1.5 g daily, as presently envisioned.

The invention will now be described in greater operational detail by the following examples, which are provided to illustrate but not to limit the concepts and the practices disclosed.

Female sprague-Dawley rats weighing between 220 and 250 g were used in the procedures described in all the examples. They were housed in a controlled environment with lights on each day between 0600 and 1800 hours, and maintained on an ad libitum schedule of food and water for one week prior to any experiment. Twenty-four hours before an experiment, they were deprived of food and placed in individual wire cages. All drugs administered in the experiments that are the subject of the examples were delivered by gastric intubation in 2 ml of 1% methylcellulose.

EXAMPLE 1

This example provides a controlled comparison of the gastric ulceration capacity of indomethacin and aspirin, in the presence and in the absence of stress.

In this experiment, animals were assigned randomly either to a stress or a nonstress condition. The stress condition applied was a modification of multiple-stress procedure described by Levine (1967) and entailed individually restraining rats for two hours in commercially available plexiglas devices placed in an environmental chamber maintained at 5° C. [See R. J. Levine, *Peptic Ulcer*, (Ed. C. J. Pfeiffer), pages 92–97, Lippincott (1971); E. C. Senay and R. J. Levine, *Proc. Soc. Exp. Biol. Med.* 124, 1221–1223 (1967)]. Within each condition, the animals received orally one of several doses of aspirin or indomethacin. Thirty minutes after drug administration, the animals were subjected either to two hours of cold restraint (stress condition) or returned to their home cages (non-stress condition) for the same duration of time.

At the end of the two-hour period, the animals were sacrificed by decapitation and blood was collected from the trunk in chilled heparinized tubes and centrifuged. The plasma was separated and frozen for subsequent fluorometric assay of corticosterone [Vernikos-Danellis J. et al. Changes in adrenal corticosterone concentration in rats. Method of bioassay for ACTH. Endocrinology, 1966, 79, 624–630]. The stomach then was removed from the animal, cut along the greater curvature, opened, rinsed with tap water and pinned in a standard position for microscopic examination and scoring of ulcers. Ulcers measuring less than 1 mm were not scored. For each animal, the overall ulcer score was defined as the sum of the maximum continuous lengths (in mm) of each ulcer. This scoring method was found previously to be highly reliable (Brown et al. 1976). Representative stomachs were fixed in 10% formol saline and 8$\mu$ paraffin sections from tissue blocks taken from ulcerated areas were stained with hematoxylin and eosin and examined microscopically.

Figure 2:
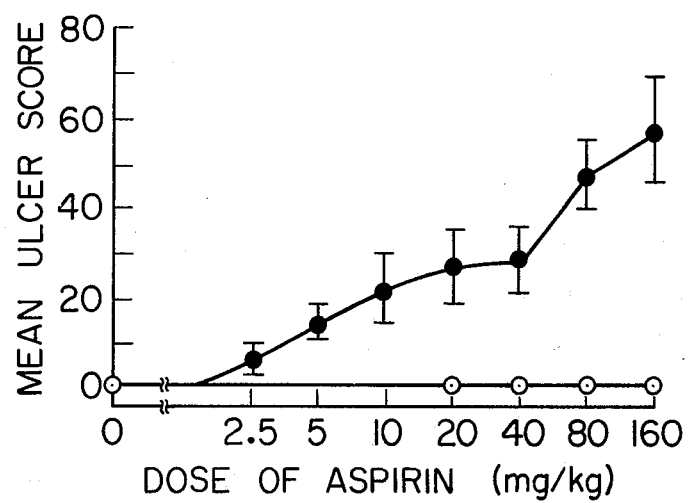
FIG. 2, provided for comparison purposes, depicts the ulcerogenic properties of aspirin under similar conditions.

The dosages of aspirin and indomethacin and the consequences of such dosages are shown in FIGS. 1 and 2 of the drawings.

As FIG. 2 indicates, there was a dramatic synergism between aspirin and environmental stress in the production of gastric ulceration. Control stressed animals that received only the methylcellulose vehicle (zero dose of aspirin) essentially did not ulcerate (ulcers generally were less than 1 mm) and even very high doses of aspirin failed to produce appreciable gastric damage in the absence of stress. However, in conjunction with stress, the administration of low doses (2.5 mg/kg) did result in minor ulceration (FIG. 1). Increasing the dose to 20 mg/kg resulted in substantial ulceration in these animals with a mean score of 27.4. Maximum ulceration was obtained with 160 mg/kg of aspirin, yielding a mean ulcer score of 56.9. Still higher doses produced no further increase in gastric ulceration. The dose-response relationship was highly significant as tested with a one-way analysis of variance (F=4.88; df=63; p<0.01).

Similarly, in the absence of stress, high doses (12 mg/kg) of indomethacin failed to produce gastric ulcers as shown in FIG. 1. However, the lowest dose of indomethacin administered (1.5 mg/kg) produced appreciable gastric damage in stressed rats. Increasing the dose to 12 mg/kg resulted in a mean ulcer score of 28.2. Still higher doses produced no further increase in ulceration. The dose-response relationship was highly significant as tested with a one-way analysis of variance (F=7.35; df=4.45; p<0.001). The difference between the maximum ulcer scores produced by indomethacin and aspirin was also significant (p<0.05).

The dose-response relations for aspirin and indomethacin appear to differ in several respects. First, the maximum response to aspirin is more than twice that for indomethacin. Second, the dose-response relation for aspirin rises gradually over about a 2 log unit range, whereas that for indomethacin rises abruptly over less than 1 log unit.

Since both stress and high doses of aspirin are known to individually elevate the level of corticosteroids and since corticosteroids are known to be ulcerogenic, an attempt was made to determine whether the ulceration attributed to either indomethacin or aspirin could have been caused in part by an augmented adrenocortical response.

Mean plasma corticosterone levels were therefore determined on the two-hour blood samples earlier mentioned and the results of the tests are shown in the following table.

TABLE 1
EFFECT OF ANTI-INFLAMMATORY AGENTS ON MEAN PLASMA CORTICOSTERONE LEVELS[a] IN STRESSED AND NONSTRESSED RATS

| Dose (mg/kg) | Experimental Condition | |
|---|---|---|
| | Aspirin (n = 9) | Aspirin + Stress (n = 9) |
| 0 | 32.0 ± 3.7 | 134.1 ± 5.3 |
| 20 | 27.3 ± 7.2 | 138.9 ± 4.4 |
| 40 | 26.9 ± 5.0 | 137.2 ± 3.9 |
| 80 | 34.7 ± 5.9 | 137.3 ± 7.1 |
| 160 | 63.9 ± 7.7 | 126.0 ± 9.2 |
| | Indomethacin (n = 10) | Indomethacin + Stress (n = 10) |
| 0 | 21.1 ± 3.7 | 134.3 ± 5.0 |
| 1.5 | 23.6 ± 4.9 | 132.4 ± 5.7 |
| 3.0 | 21.1 ± 5.2 | 138.5 ± 3.9 |
| 6.0 | 29.0 ± 5.9 | 136.5 ± 3.5 |
| 12.0 | 32.9 ± 6.5 | 139.4 ± 8.7 |

[a]Mean ± S.E. ($\mu$g/100 ml of plasma)

From the table, it can be readily seen that corticosterone levels at the end of the two-hour period were markedly elevated in rats under stress. However, neither indomethacin nor aspirin produced any significant additional increase in corticosterone in these animals. Thus, increasing gastric damage produced by the drugs in the stressed rats was not associated with an increase in circulating corticosterone. The mean corticosterone levels of nonstressed animals were also unaffected by the drugs, except at the highest dosage tested. This latter rise in corticosterone was not accompanied by any corresponding increase in gastric ulceration.

EXAMPLE 2

In this example the size and regional distribution of ulceration produced by indomethacin and aspirin are compared.

For the experiment, animals were asigned randomly to groups receiving either 12 mg/kg of indomethacin or 20 mg/kg of aspirin. The doses administered were selected on the basis of results of the first experiment (FIGS. 1 and 2) to give approximately the same mean ulcer score. Thirty minutes after drug administration, the animals were put in cold restraint for two hours. At the end of the stress period, the animals were sacrificed and ulcers were scored a described in Example 1.

The gastric ulcers produced by aspirin and indomethacin in stressed rats appeared as black or brown punctate or elongate regions with sharply defined edges. Microscopic examination of hematoxylin and eosin stained paraffin sections taken from regions of ulceration revealed necrosis of the gastric mucosa sometimes extending to, but never through, the muscularis mucosa.

Figure 3:
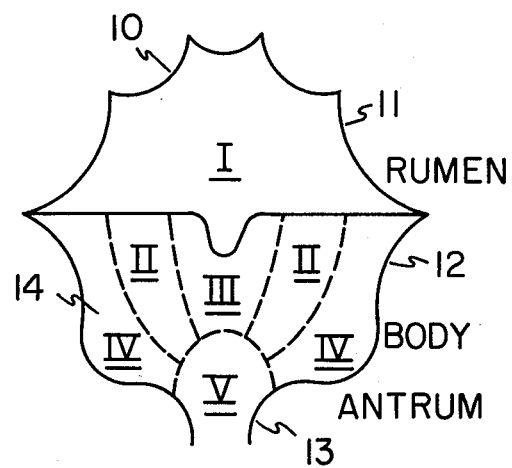
FIG. 3 shows a rat stomach which has been opened and spread out to locate the various zones where ulcers may be produced.

In stressed animals, high doses of aspirin ($\geq 80$ mg/kg) produce very large ulcers (see FIG. 1b, Brown et al., 1976) generally not seen with very high doses ($\geq 24$ mg/kg) of indomethacin. However, at lower doses, for a given mean ulcer score, the size as well as the regional distribution of the ulcers were similar for aspirin and indomethacin. At the doses selected, both agents produced numerous small ulcers in the range of 1.0 to 2.9 mm and only occasionally ulcers 3.0 mm or larger. Following the scoring method of Tagaki et al. [Chemical and Pharmaceutical Bulletin, 1964, 12, pages 465 to 472], the number of ulcers in each of five zones of the stomach was determined. FIG. 3 shows the anatomical divisions of a stomach which for better visualization has been opened along the greater curvature and pinned out. As can be seen from the drawing, the stomach is divided into three main areas, i.e., the rumen (11), the body (12), and the antrum (13), with each area comprising the anatomical divisions indicated (I, II, III, IV, and V). The distribution of gastric ulcers observed is shown in the following table.

TABLE 2

REGIONAL DISTRIBUTION OF GASTRIC ULCERS PRODUCED BY ASPIRIN AND INDOMETHACIN IN STRESSED ANIMALS

| | Mean Number of Ulcers | |
|---|---|---|
| Zone of Stomach | Aspirin (20 mg/kg) N = 8 | Indomethacin (12 mg/kg) N = 8 |
| I | 0.0 | 0.0 |
| II | 23.5 | 12.3 |
| III | 1.6 | 2.5 |
| IV | 15.0 | 18.0 |
| V | 0.9 | 1.3 |

As can be seen in Table 2, neither indomethacin nor aspirin caused ulcers in Zone 1, the rumen of the stomach, but both drugs induced numerous ulcers in Zones II and IV of the body. On the other hand, few ulcers were produced by either agent in Zone III of the body or Zone V, the antrum.

EXAMPLE 3

Figure 4:
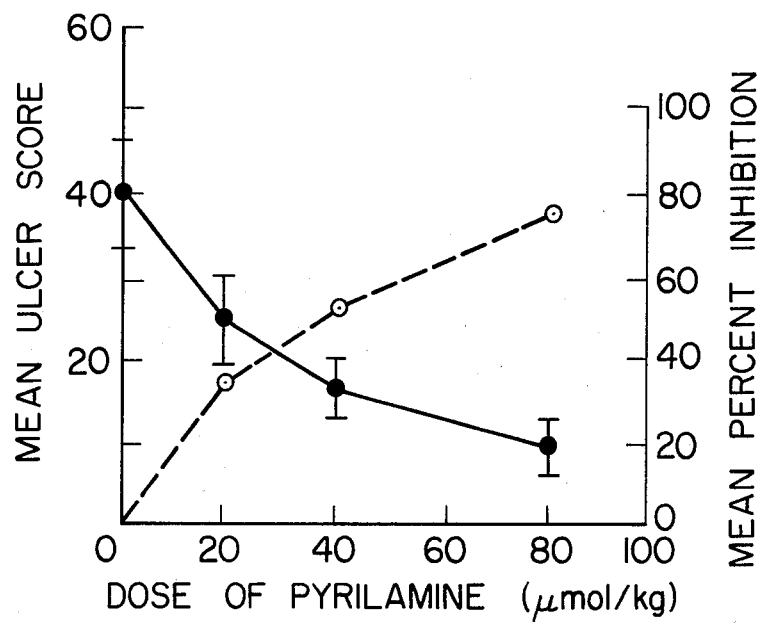
FIG. 4 illustrates the effect of an H$_1$ receptor antagonist, pyrilamine, on gastric ulceration induced by indomethacin in rats under stress.
Figure 5:
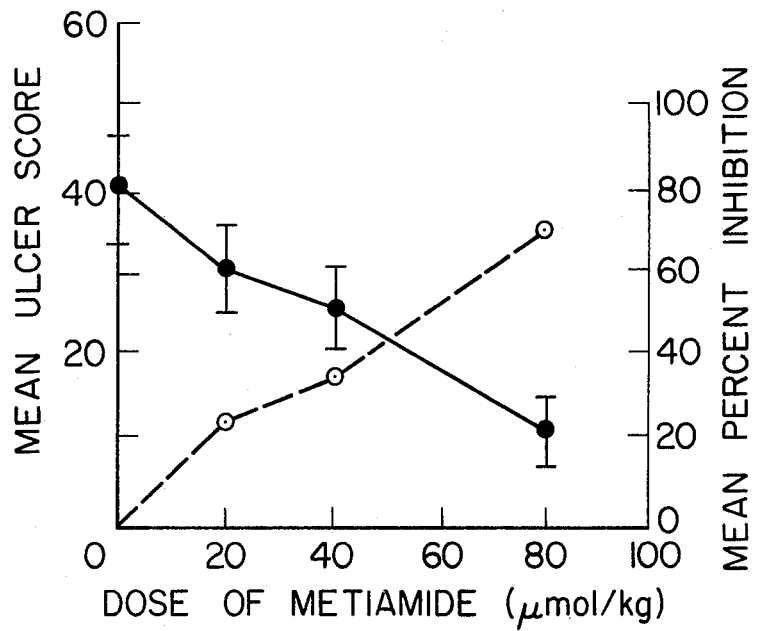
FIG. 5, on the other hand, shows the effect of an H$_2$ receptor antagonist, metiamide, under similar conditions.

In these tests to determine the effect of antihistamines on ulceration caused by the combined action of indomethacin and stress, animals again were assigned randomly to groups receiving either pyrilamine maleate or metiamide at the dosages indicated in FIGS. 4 and 5. Additionally each animal received 6 mg/kg of indomethacin. Both the antihistamine and the anti-inflammatory agent were delivered orally in the same 2 ml of methycellulose solution. Thirty minutes after drug administration each animal was subjected to two hours of cold restraint. At the end of that stress period, all animals were sacrificed by decapitation and the stomachs were removed, pinned, and scored as in Example 1.

To determine whether the antiulcerogenic properties of pyrilamine is specific to that drug, other animals were treated in the same manner with a structurally different $H_1$ receptor blocker, promethazine.

The effectiveness of the antihistamines in inhibiting gastric ulceration produced by indomethacin in rats under stress is shown in FIGS. 4 and 5, and in Table 3.

As can be seen from the curves plotted, the dose-response curves for pyrilamine and metiamide are very similar. In the absence of antihistamine, the mean ulcer score in both control groups was somewhat higher than expected from the results of the first experiment, probably reflecting monthly variations to susceptibility to gastric ulceration [Wilson, T. R., Monthly Variations in the Severity of Experimental Stress Ulcers in Rats. In C. J. Pfeiffer (Ed.) Peptic Ulcer, Philadelphia: J. C. Lippincott, 1971]. At the lowest dose of pyrilamine administered, the mean ulcer score was reduced 38%. Similarly the lowest dose of metiamide reduced the mean ulcer score 24%. Increasing the dose of both antihistamines produced further reductions in ulcer severity resulting in a mean score of 10.1 and 11.2 for pyrilamine and metiamide, respectively. The dose-response relationship for these antihistamines was highly significant as tested by a one-way analysis of variance (Pyrilamine: $F=6.47$; $df=3,53$; $p<0.001$; Metiamide: $F=4.65$; $df=3,52$; $p<0.01$). The $ID_{50}$ was roughly 35 $\mu$mol/kg for metiamide.

TABLE 3

THE ANTIULCER EFFECTS OF METIAMIDE AND PROMETHAZINE ON INDOMETHACIN PRODUCED ULCERS IN STRESSED RATS

| Condition | Mean ± SEM | % Reduction |
|---|---|---|
| IND | 46.2 ± 6.8 | |
| IND + MET | 14.3 ± 2.5 | 69.0 |
| IND ± PROM | 19.6 ± 4.9 | 57.0 |

*$t(15,15) = 4.25$, $p<.005$
**$t(15,15) = 3.06$, $p<.005$

As can be seen further from Table 3, the $H_1$ receptor antagonist, promethazine, achieved reductions in gastric ulceration that are comparable to those produced by metiamide. The latter tests were carried out with high doses of antihistamine (80 $\mu$mol/kg) in stressed rats receiving 6 mg/kg of indomethacin.

EXAMPLE 4

The procedure of Example 3 was followed except that the antihistamine used to counteract the gastric effects of indomethacin was cimetidine. Indomethacin was administered at the usual rate of 6 mg/kg while the cimetidine dosages tested were 20 and 80 $\mu$mol/kg, eight stressed rats being used for each level of antihistamine.

The mean ulcer score for the control group was determined to be 49 with a decrease to 33 for the lower dosage and to 21 for the higher dosage of cimetidine. In other words, the mean ulcer score was reduced 32.6% at the lower dose of cimetidine administered, and 57% at the higher dose.

As the present results clearly demonstrate, a dramatic synergism occurs between acute stress and moderate dosages of anti-inflammatory agents in the production of gastric ulceration (FIGS. 1 and 2). The difference between the effects of aspirin and indomethacin cannot be attributed, however, to any additional effects in plasma corticosterone levels. The results do indicate that the level of plasma corticosterone was greatly increased by the stress procedure, but neither anti-inflammatory agent was found to produce any additional increase in corticosterone level.

As to the effect of antihistamines on gastric ulceration caused by a combination of anti-inflammatory agents and stress, it was rather surprising to discover that not only metiamide could reduce ulceration, but that the $H_1$ receptor antagonist, pyrilamine and promethazine, also did. Earlier published data (Brown et al. 1976) showed that the latter drugs do not function in that capacity with aspirin. These data suggest generally that the mechanism of action of indomethacin differs, in an unknown manner, from that of aspirin.

Although the invention has been described in terms of certain preferred embodiments, it is contemplated that the man skilled in the art may carry out modifications that will remain within the spirit and the scope of the following claims.

What is claimed is:

1. A process for reducing gastric ulceration caused by the administration of indomethacin to a mammal under stress, which comprise administering to said mammal an antihistamine drug selected from the group consisting of metamide and cimetidine, said antihistamine drug being administered at the rate of about 0.2 to 1.5 g for each 0.025 to 0.200 g dose of indomethacin.

2. A pharmaceutical composition for reducing gastric ulceration caused by the administration of indomethacin to a mammal under stress, comprising indomethacin and about 0.2 to 1.5 g of an antihistamine drug selected from the group consisting of metamide and cimetidine, for each 0.025 to 0.200 g dose of indomethacin.

* * * * *